(12) United States Patent
Swann

(10) Patent No.: US 8,523,946 B1
(45) Date of Patent: Sep. 3, 2013

(54) STAND-ALONE SPINAL CAGE

(76) Inventor: Karl W. Swann, San Antonio, TX (US)

(*) Notice: Subject to any disclaimer, the term of this patent is extended or adjusted under 35 U.S.C. 154(b) by 0 days.

(21) Appl. No.: 13/022,305

(22) Filed: Feb. 7, 2011

Related U.S. Application Data

(60) Provisional application No. 61/302,088, filed on Feb. 6, 2010.

(51) Int. Cl.
*A61F 2/44* (2006.01)

(52) U.S. Cl.
USPC ........................... 623/17.16; 623/17.11

(58) Field of Classification Search
USPC ............... 606/246–249; 623/17.11–17.16
See application file for complete search history.

(56) References Cited

U.S. PATENT DOCUMENTS

| | | | |
|---|---|---|---|
| 5,658,335 | A | 8/1997 | Allen |
| 6,102,950 | A | 8/2000 | Vaccaro |
| 6,113,638 | A | 9/2000 | Williams et al. |
| 6,447,547 | B1 | 9/2002 | Michelson |
| 6,527,803 | B1 | 3/2003 | Crozet et al. |
| 7,704,278 | B2 | 4/2010 | Moskowitz et al. |
| 7,963,995 | B2 | 6/2011 | Richelsoph |
| 8,062,374 | B2 | 11/2011 | Markworth et al. |
| 8,105,358 | B2 | 1/2012 | Phan |
| 2005/0049590 | A1* | 3/2005 | Alleyne et al. .................. 606/61 |

OTHER PUBLICATIONS

FDA, "FDA Clears LDR's ROI-C," Walter Eisner, Jul. 22, 2009, 2 pages.
"The Eclipse-L Vertebral Interbody Lumbar Spacer System," Apollo Spine, 4 pages. 2012.

* cited by examiner

*Primary Examiner* — Eduardo D Robert
*Assistant Examiner* — Christina Negrellirodriguez
(74) *Attorney, Agent, or Firm* — Jackson Walker, LLP

(57) ABSTRACT

A spinal cage device for fusion of spinal vertebrae comprising a cage body having a cavity defined by upper, lower, and side walls; a piston selectively insertable into the cavity through a side wall, the piston having at least one angled surface; at least one channel extending through at least one of the upper wall and the lower wall; at least one fastening member moveable within the at least one channel between a first disengaged position and a second engaged position; and wherein in second engaged position the at least one fastening member is held substantially stationary relative to the cage body by contact with the piston. According to one aspect of the invention, the device includes a locking means for supplementing fixation of the piston to the cage body.

32 Claims, 18 Drawing Sheets

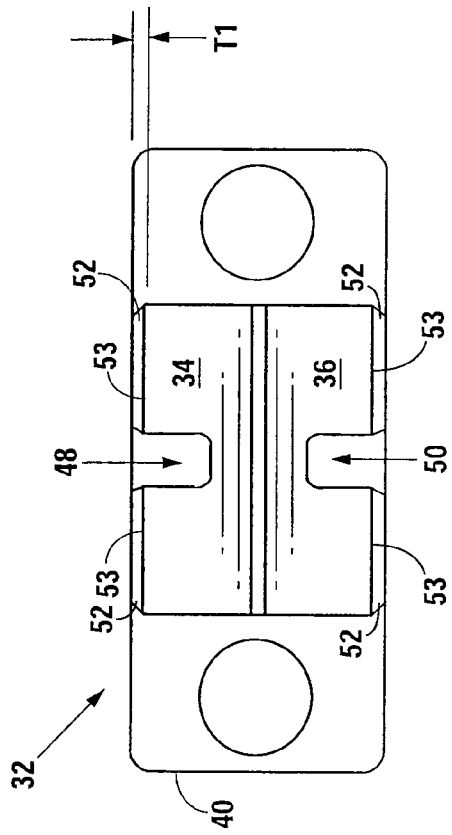
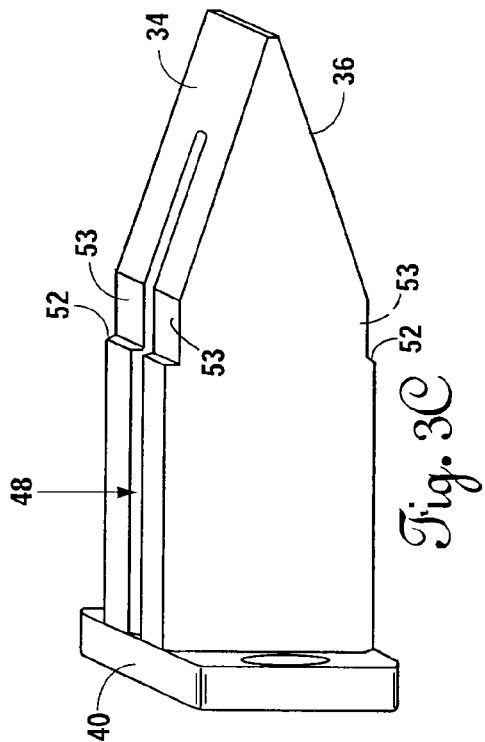
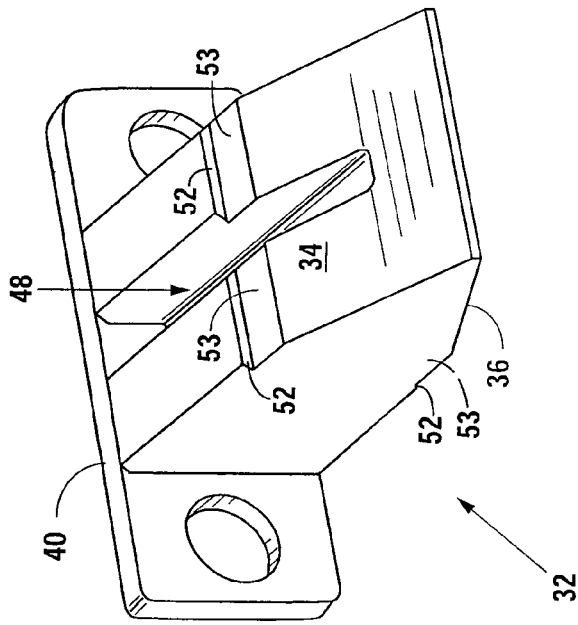

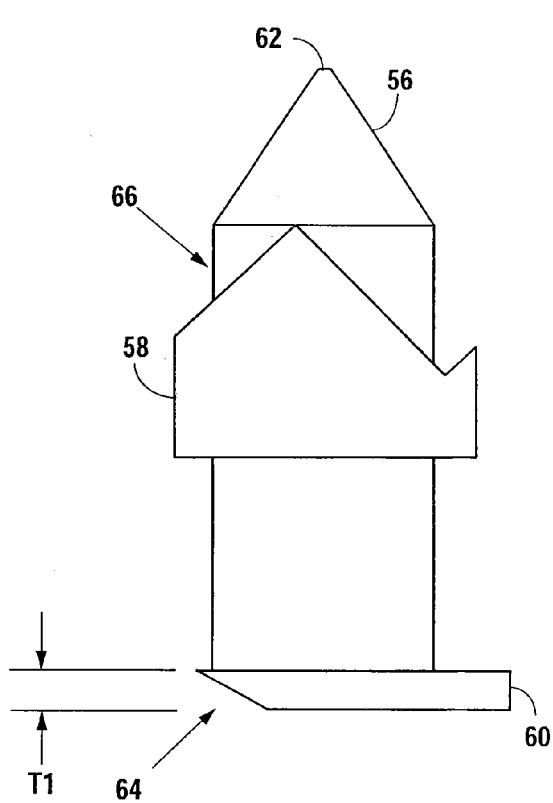
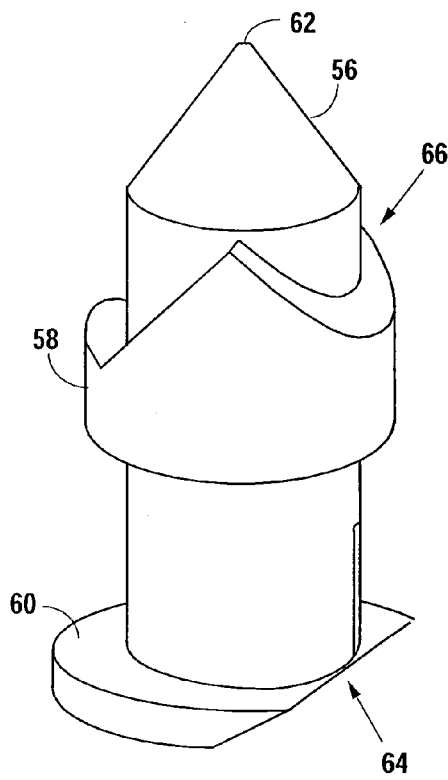
Fig. 4A
Fig. 4B

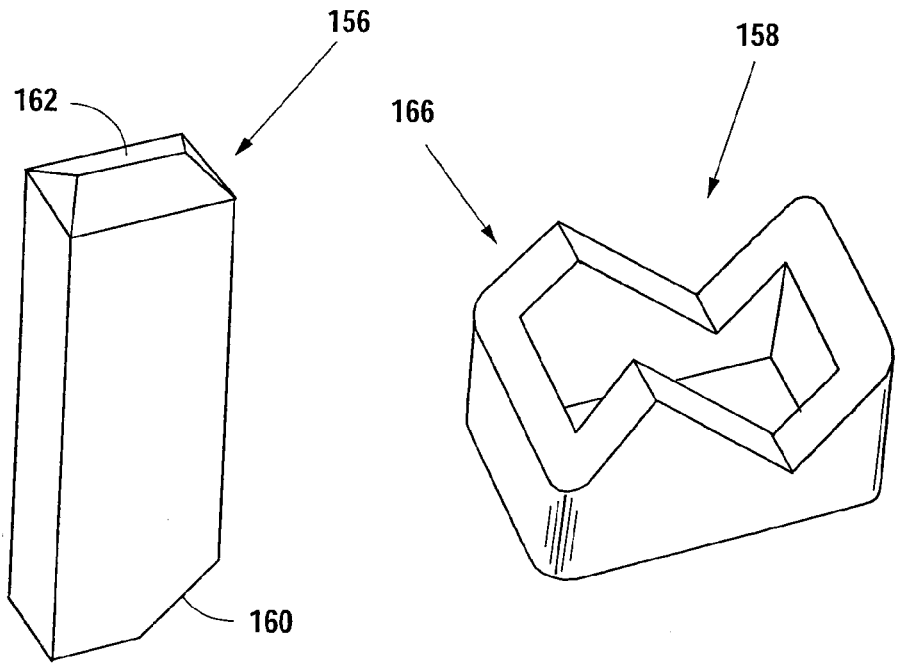
Fig. 9A
Fig. 9B
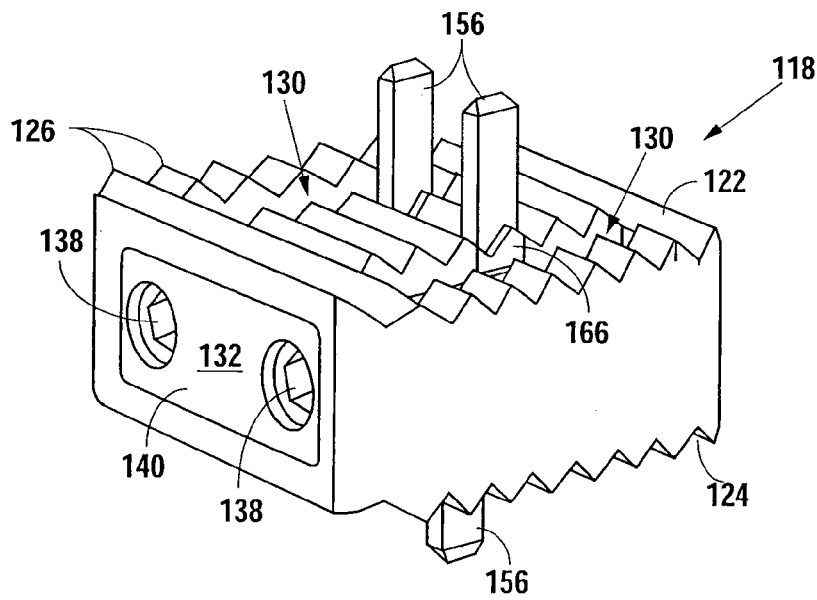
Fig. 10

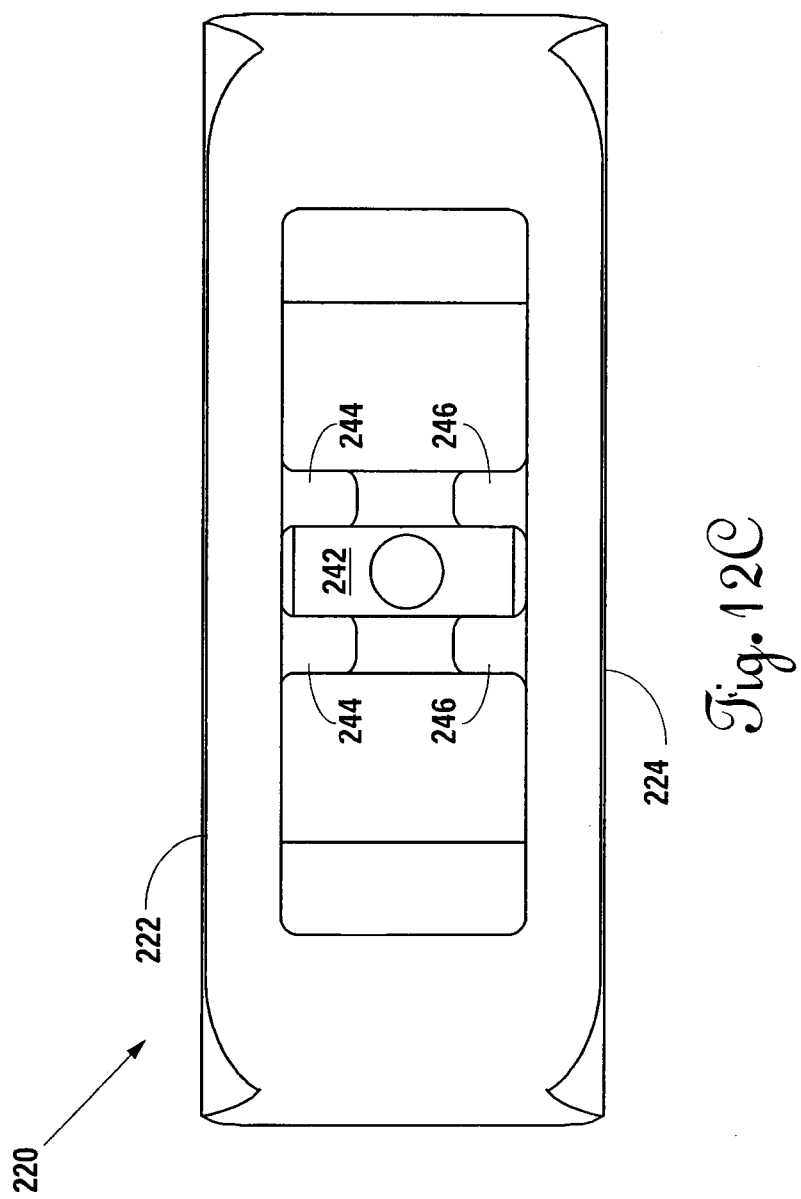

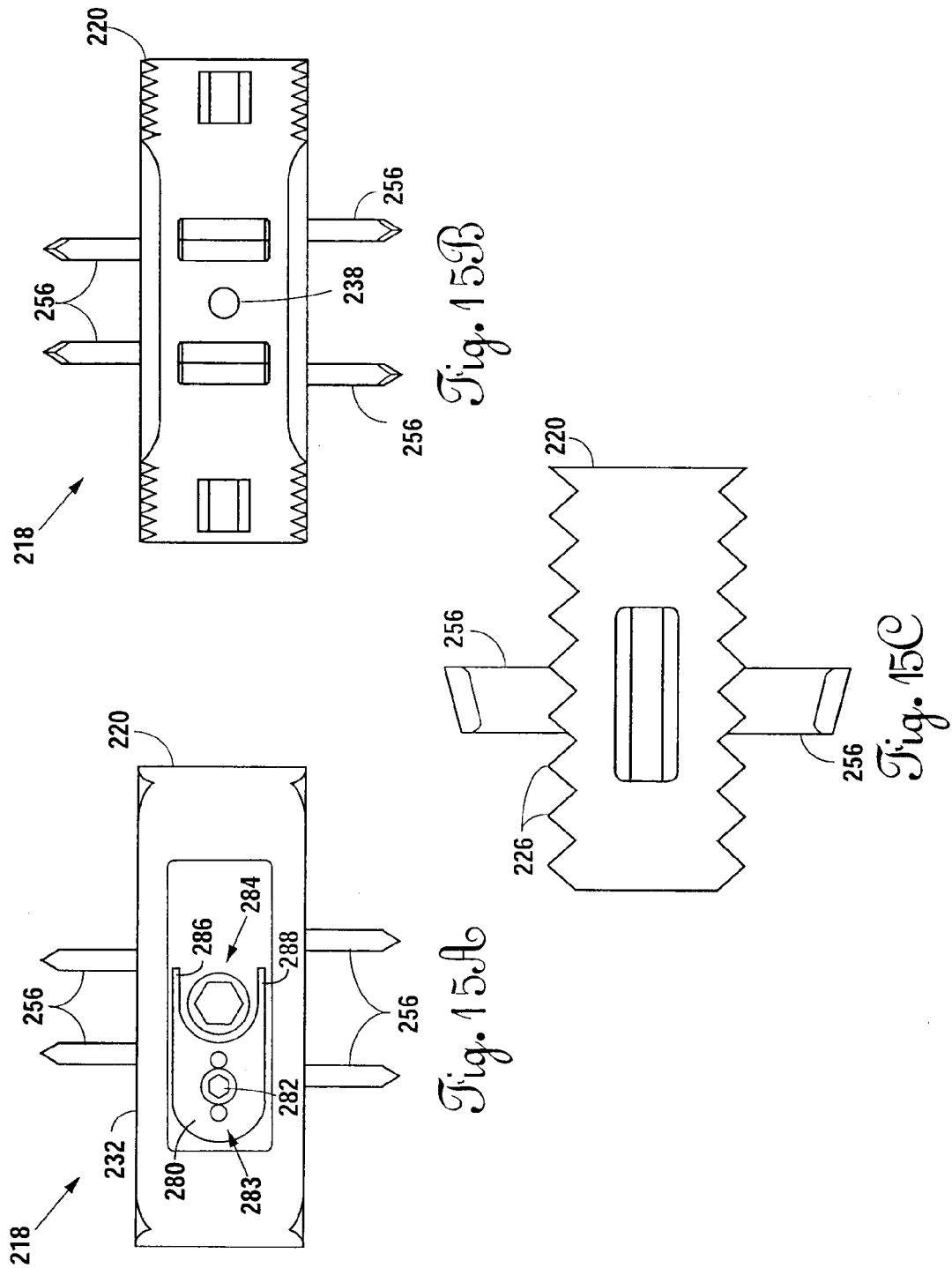

US 8,523,946 B1

STAND-ALONE SPINAL CAGE

CROSS REFERENCE TO RELATED APPLICATIONS

This original nonprovisional patent application claims the benefit of U.S. provisional application Ser. No. 61/302,088, filed Feb. 6, 2010 and entitled "Stand-Alone Spinal Cage," and which is incorporated by reference herein.

STATEMENT REGARDING FEDERALLY SPONSORED RESEARCH OR DEVELOPMENT

Not applicable.

BACKGROUND OF THE INVENTION

1. Field of the Invention

The present invention relates to a spinal cage device. More specifically, the present invention is a stand-alone spinal cage designed to obviate the need for an accompanying anterior spinal plating systems.

2. Description of the Related Art

Traditional spinal cages are often implanted with anterior plating to prevent movement of the spinal cage over time. The present invention is a stand-alone spinal cage that obviates the need to use anterior spinal plating systems.

BRIEF SUMMARY OF THE INVENTION

The present invention is a spinal cage device for fusion of spinal vertebrae comprising a cage having a cavity defined by upper, lower, and side walls; a piston selectively insertable into the cavity through a side wall, the piston having at least one angled surface; at least one channel extending through at least one of the upper wall and the lower wall; at least one fastening member moveable within the at least one channel between a first disengaged position and a second engaged position; and wherein in second engaged position the at least one fastening member is held substantially stationary relative to the cage by contact with the piston. According to one aspect of the invention, the device includes a locking means for supplementing fixation of the piston to the cage by the internal screw(s). According to another aspect of the invention, the fastening members (e.g., nails or pins) of the device are porous to allow bone growth therethrough.

BRIEF DESCRIPTION OF THE SEVERAL VIEWS OF THE DRAWINGS

FIGS. 3A-3C depict various views of the piston of the first embodiment.

FIGS. 4A-4B shows a fastening member and bushing of the first embodiment.

FIGS. 9A and 9B depict a fastening member and bushing, respectively, of the second embodiment.

FIG. 10 is a rear isometric view of the second embodiment.

FIG. 12C is a side elevational view of the third embodiment of Applicant's invention.

FIGS. 15A-15C are rear, front, and side elevations, respectively, of the third embodiment in the engaged state.

DETAILED DESCRIPTION OF THE INVENTION

The present invention may be used in the cervical, lumbar, or thoracic regions of the spine. Some components of the embodiment described herein, such as the cage bodies, are preferably made of biocompatible OXPEKK, a poly-ether-ketone-ketone sold under the registered trademark of Oxford Performance Materials, Inc., Enfeld, Conn., USA. Alternative embodiments contemplate fabrication from biocompatible PEEK (poly-ether-ether-ketone). OXPEKK has approximately one-and-a-half to two times the compressive strength of PEEK, and therefore may be suited for constructing the cage body.

In addition to the foregoing, it should be noted that, while the embodiments described herein are solid bodies, they may also be formed as porous bodies, as described in U.S. application Ser. No. 612/952,788 (filed Nov. 23, 2010), entitled "Spinal Cage Device" and incorporated by reference herein.

While the terms "upper," "lower," "front," "rear," and similar terms are used throughout this document, it should be expressly understood that such are simply terms of convenience only to aid in description of the invention, and the orientation of the invention disclosed herein after during implantation is primarily within the surgeon's discretion.

First Embodiment

Figure 1:
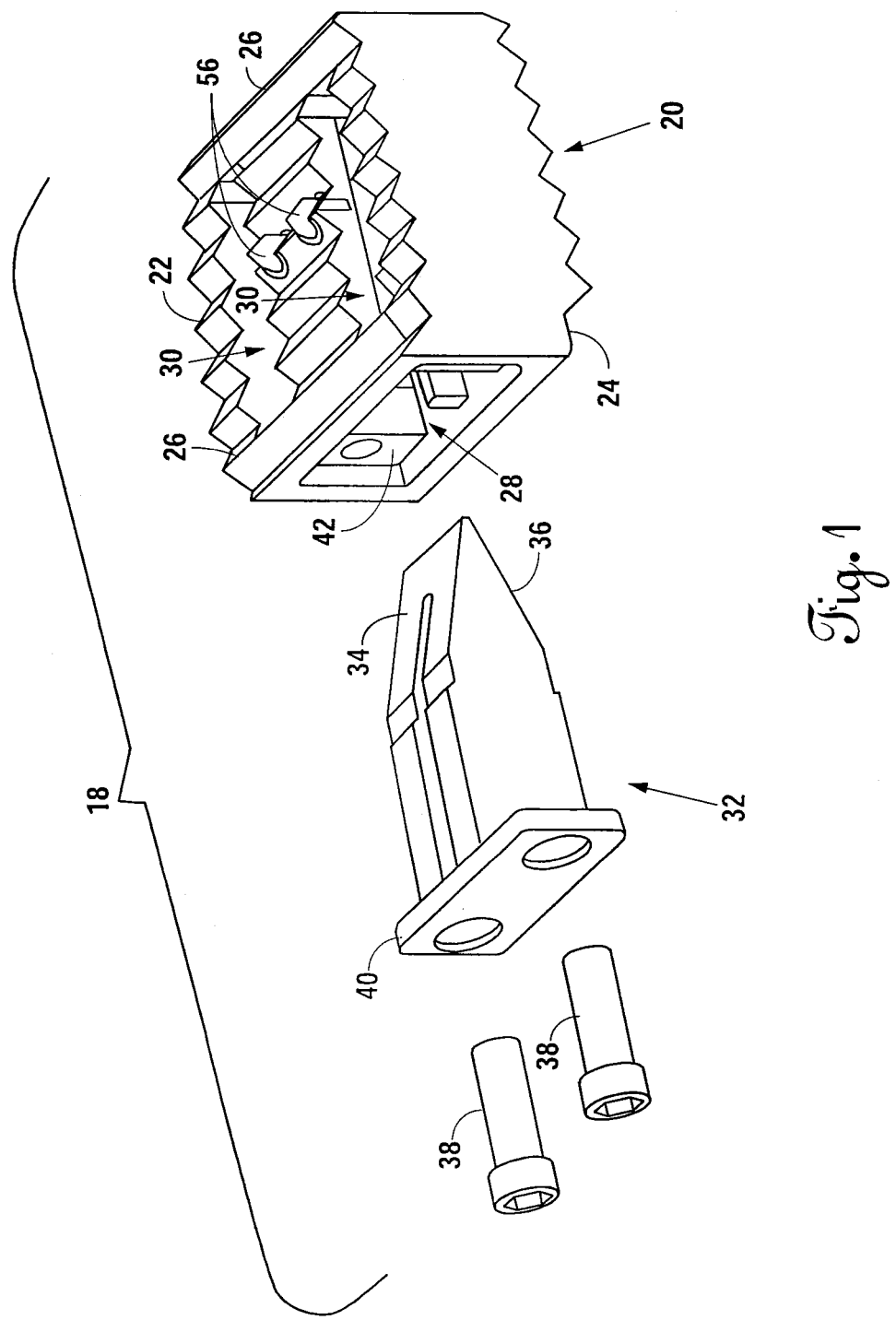
FIG. 1 is an assembly view of a first embodiment of the invention.

A first embodiment 18 of the invention is shown in FIGS. 1-5. FIG. 1 is an assembly view of the first embodiment 18, which comprises a cage body 20 having upper and lower walls 22, 24 with ridges 26. Upper and lower walls 22, 24 partially define a cavity 28 of the cage body 20. Openings 30 through the upper and lower walls 22, 24 provide access to the cavity 28 to allow for bone growth thereinto from adjacent vertebrae. A piston 32 having upper and lower angled surfaces 34, 36 is insertable into the cavity 28 through a piston opening in the posterior sidewall of the cage body 20 to engage and drive nails 56. Piston screws 38 may thereafter be inserted through a piston faceplate 40 and secured to screw mounts 42 located in the cavity 28 near the posterior opening.

Figure 2C:
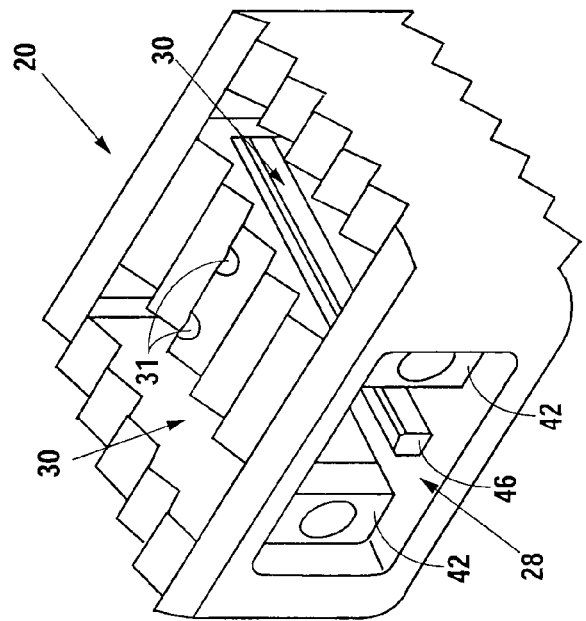
FIG. 2C is a rear isometric view of the first embodiment.
Figure 2A:
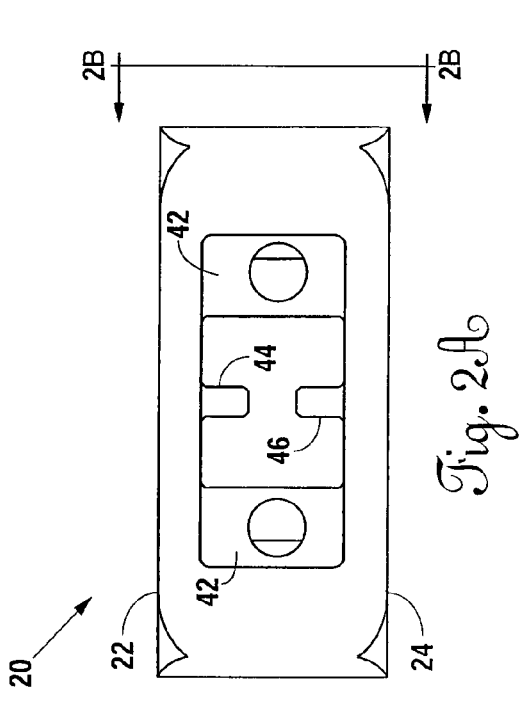
FIG. 2A is a front view of the first embodiment.
Figure 2B:
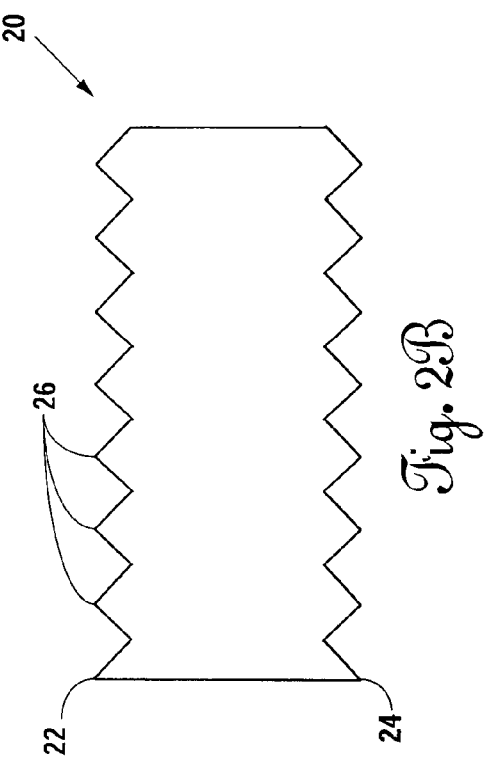
FIG. 2B is side elevation through line 2B-2B of FIG. 2A.

FIGS. 2A-2C show the cage body 20 is greater detail. Upper and lower rails 44, 46 extend along the length of, and protrude into the cavity 28 from, the upper and lower walls 22, 24, respectively. Screw mounts 42 are located near the posterior side of the cavity 28. Openings 30 through the upper wall 22 and lower wall 24 provide access to the cavity 28 to allow for bone growth thereinto from adjacent vertebrae. Cylindrical channels 31 are located between the two openings 30 and provide a cylindrical path through the upper wall 22 to the cavity 28. A pair of cylindrical channels (not shown) is disposed through the lower wall in similar fashion and aligned with the upper channels 31.

FIGS. 3A-3C show the piston 32 of the first embodiment in greater detail. The piston 32 has upper and lower angled planar surfaces 34, 36 approximately sixty degrees apart. Upper and lower grooves 48, 50 are formed longitudinally along the piston 32 and extend between the faceplate 40 and the upper and lower angled planar surfaces 34, 36. The grooves 48, 50 are alignable with, and during insertion guide the piston 32 along, upper and lower rails 44, 46 (see FIG. 2A), respectively, of the cage body 20. Shoulders 52 are formed in the piston body having a thickness T1. Engagement surfaces 53 are located between the shoulders 52 and the angled surfaces 34, 36

FIGS. 4A and 4B show a titanium nail 56 and bushing 58 of the first embodiment in greater detail. The nail 56 is generally cylindrical and has a nail head 60 of thickness T1 at a proximal end and tapers to a point 62 at the distal end. The nail head 60 has an angled portion 64 corresponding to the angled surfaces 34, 36 of the piston 32 (see FIGS. 3A-3C). The upper end 66 of the bushing 58 corresponds in shape to the upper wall 22 (see FIGS. 2A-2C) such that, when assembled, the bushing 58 is flush with the ridges 26 of the upper surface of the cage body 20 (see, e.g., FIG. 5A).

Figure 5B:
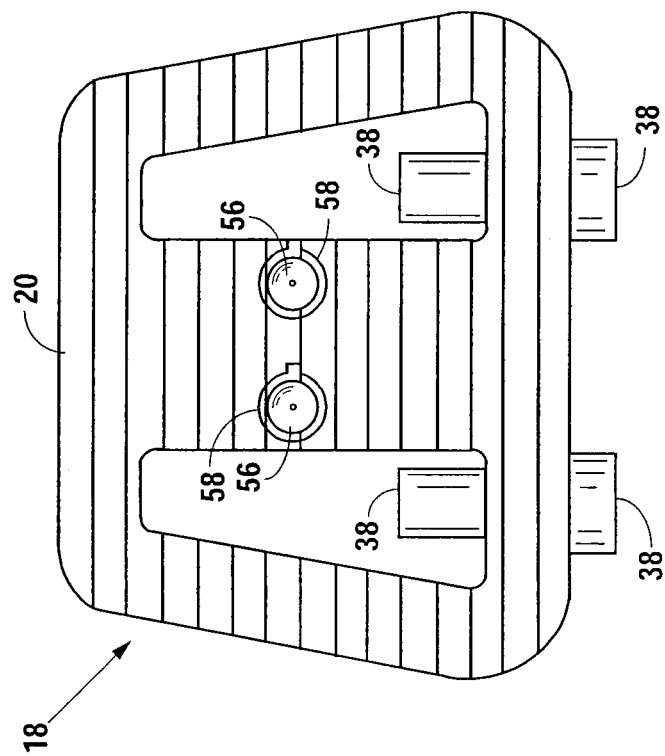
FIGS. 5A and 5B are a rear isometric and a top elevation view, of the first embodiment.
Figure 5A:
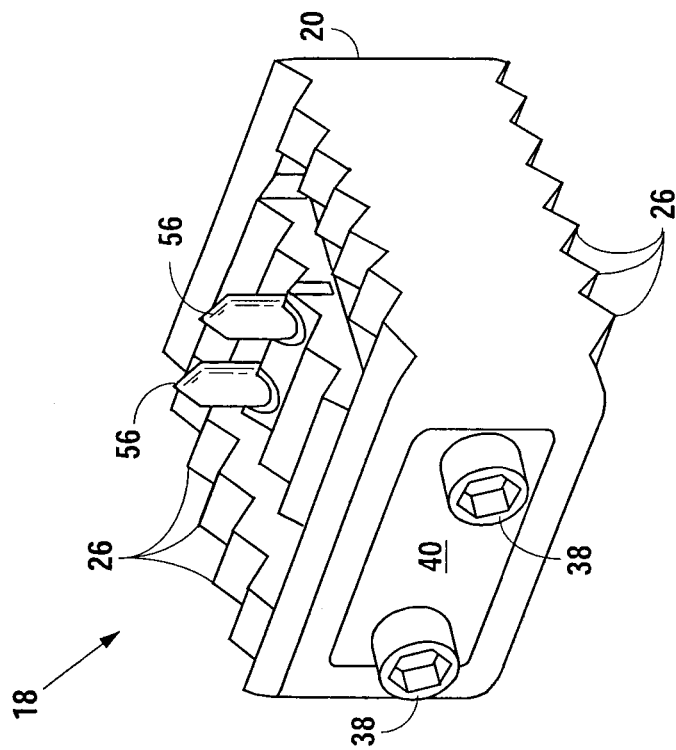
Figure 6:
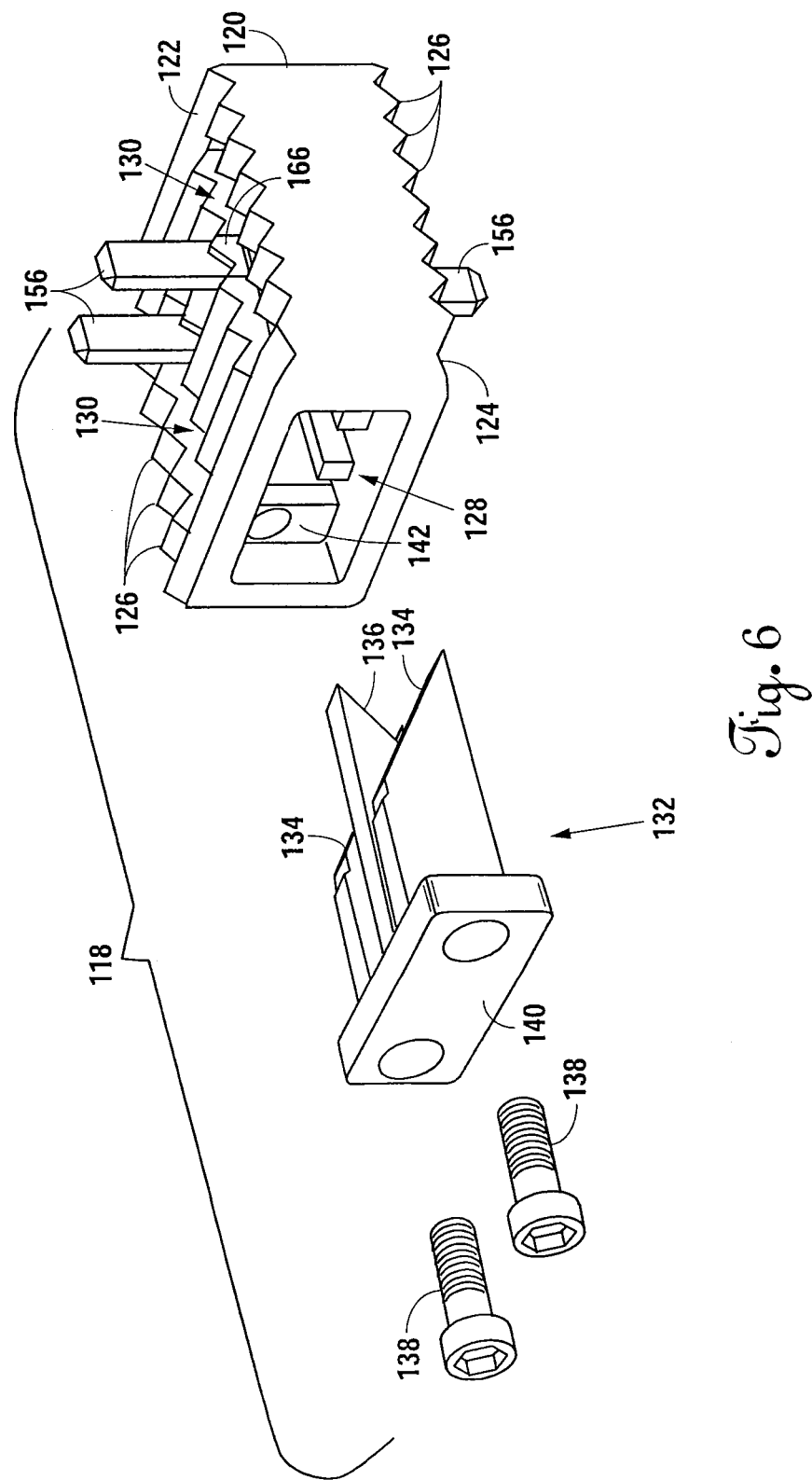
FIG. 6 is an assembly view of a second embodiment of the invention.

FIG. 5A and FIG. 5B are an isometric view and a top elevation view, respectively, of the first embodiment 18 with the nails 56 in a second engaged position. During implantation, the angled portions 60 of the nail heads 60 (see FIGS. 4A-4B) are contacted by and become flush with the angled surfaces 34, 36 of the piston 32 (see FIGS. 3A-3C), which, as the piston 32 is inserted further into the cavity 28, causes the nails 56 to move upwardly through the channels 31. In this manner, engagement of the upper angled surface 34 with the nail head 60 causes movement of the piston 32 into the cavity 28 to drive the nail 56 into the adjacent vertebra above the embodiment 18. Similarly, engagement of the lower angled surface 36 with nail heads causes movement of the piston 32 into the cavity 28 to drive lower nails (not shown) into the adjacent vertebra below the embodiment.

After complete insertion of the piston 32, each nail head 60 becomes flush with the corresponding engagement surface 53 to prevent the nail 56 from receding back into the cavity 28. This ensures fastening of the nail 56 to adjacent bone matter. The upper and lower rails 44, 46 (see FIGS. 2A, 2C) occupy the upper and lower grooves 48, 50, respectively, to ensure proper alignment of the piston 32 within the cavity 28. The ridged bushings 58 are fitted within the channels 31 in the annular space between the nail 56 and channel walls to facilitate slidable movement of the nail 56 therein. By threading the screws 38 through the faceplate 40 and the screw mounts 42, the piston 32 is drawn into the cavity 28 and secured to the cage body 20.

Second Embodiment

A second embodiment 118 of the invention, shown in FIGS. 6-10, comprises a cage body 120 having upper and lower walls 122, 124 with ridges 126. Upper and lower walls 122, 124 partially define a cavity 128 of the cage body 120. Openings 130 through the upper and lower walls 122, 124 provide access to the cavity 128 to allow for bone growth thereinto from adjacent vertebrae. A piston 132 having upper and lower angled planar surfaces 134, 136 is insertable into the cavity 128 through a piston opening in the posterior wall of the cage body 120. Screws 138 may thereafter be inserted through a piston faceplate 140 and secured to screw mounts 142 located in the cavity 128 proximal to the piston opening.

Figure 7A:
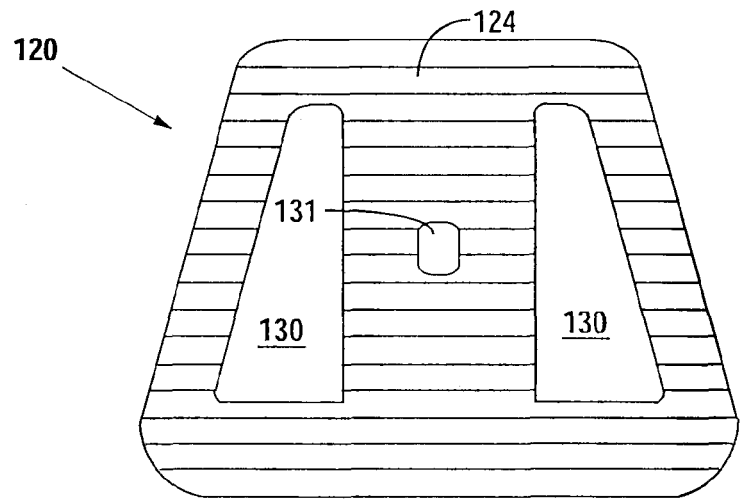
FIGS. 7A-7C are a bottom, rear elevation, and top elevation of the cage of the second embodiment.
Figure 7B:
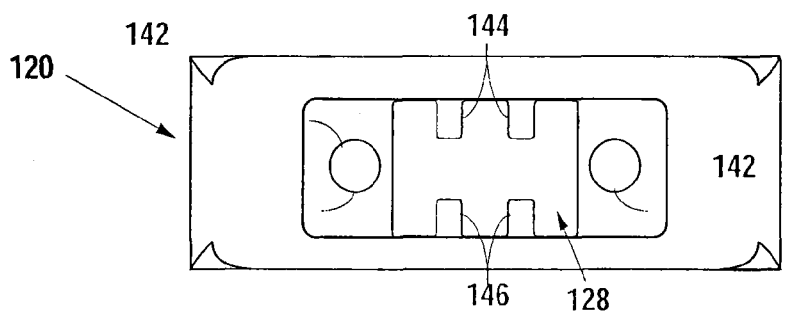
Figure 7C:
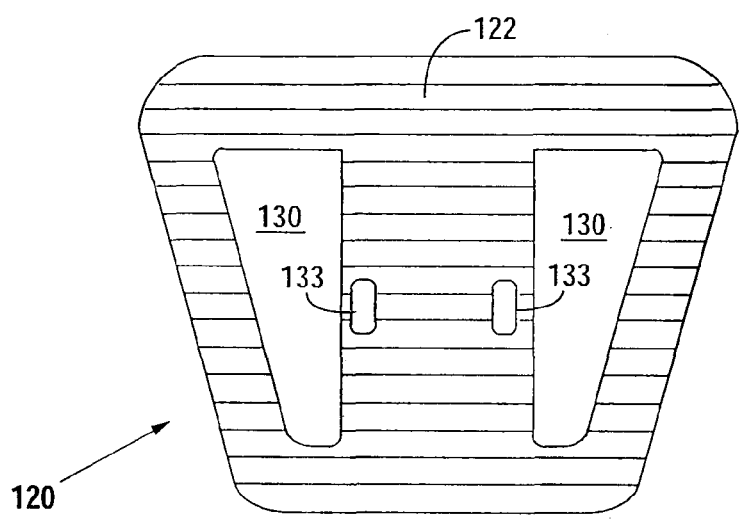

FIGS. 7A-7C show the cage body 120 of the second embodiment is greater detail. FIGS. 7A and 7C are bottom and top elevations, respectively, of the cage body 120. FIG. 7B is a rear elevation of the cage body 120. Upper and lower rails 144, 146 extend along the length of, and protrude into the cavity 128 from, the upper and lower walls 122, 124, respectively. Screw mounts 142 are located near the rear side of the cavity 128. Openings 130 through the upper and lower walls 122, 144 provide access to the cavity 128 to allow for bone growth thereinto from adjacent vertebrae. As shown in FIG. 7A, a channel 131 is located between the two openings 130 and provides a path through the lower wall 124 to the cavity. As shown in FIG. 7B, two channels 133 are located between the two openings 130 and provide a path through the upper wall 122 to the cavity 128.

Figure 8A:
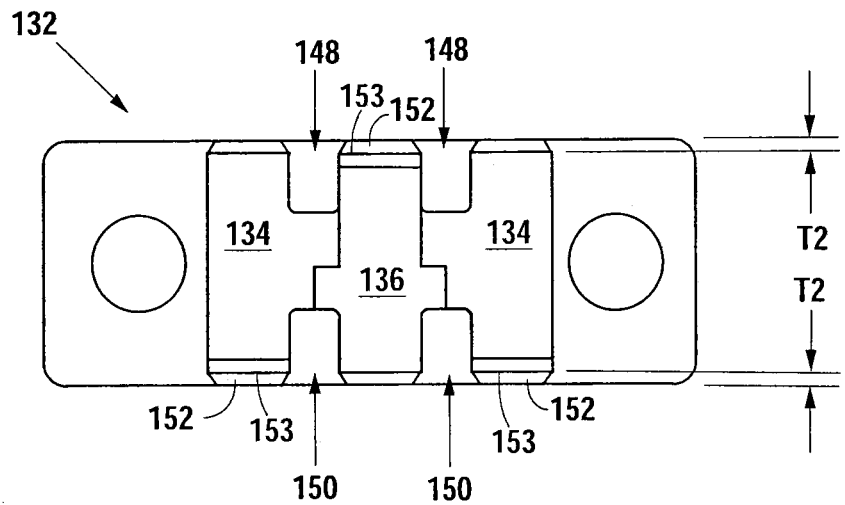
FIGS. 8A and 8B are a front elevation and a side isometric view of the piston of the second embodiment.
Figure 8B:
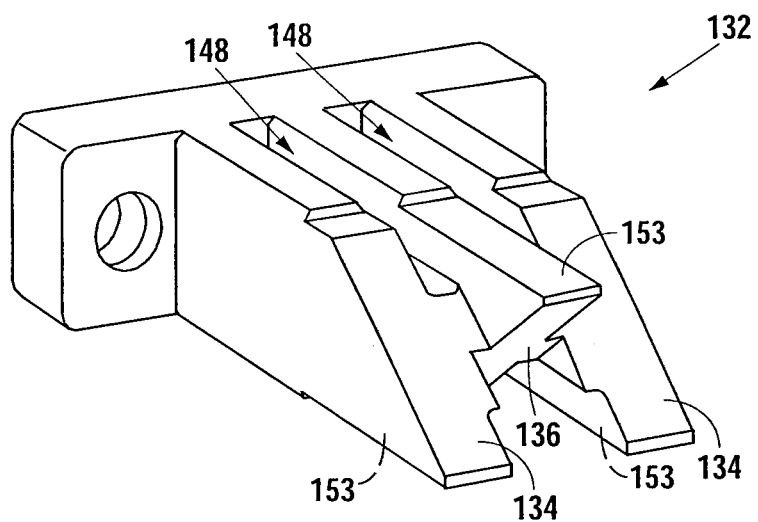
Figure 11A:
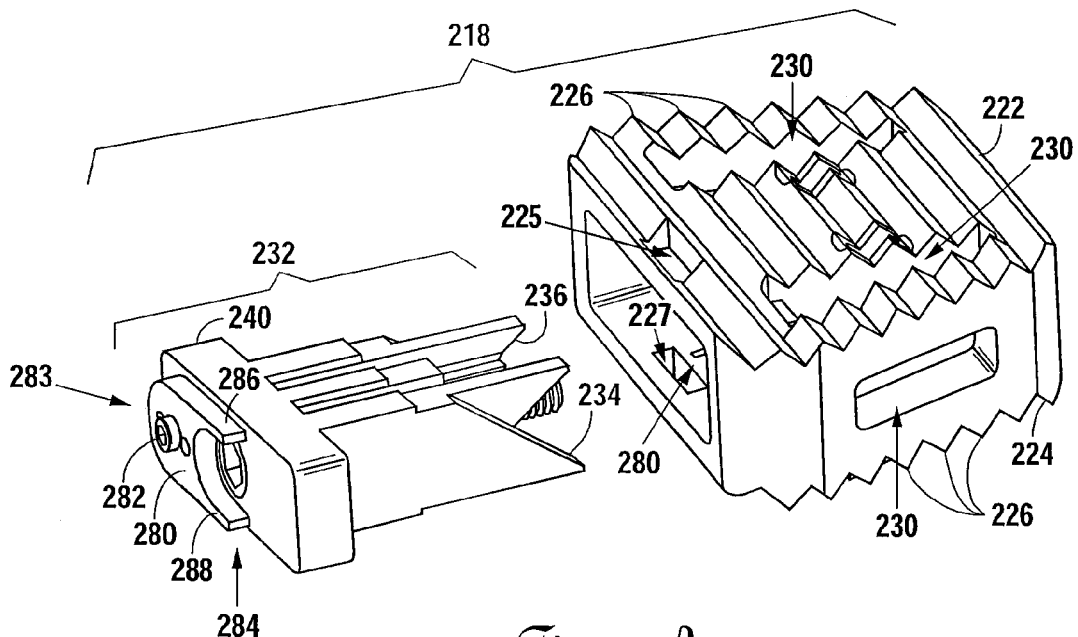
FIG. 11A is an assembly view of a third embodiment of the invention.
Figure 11B:
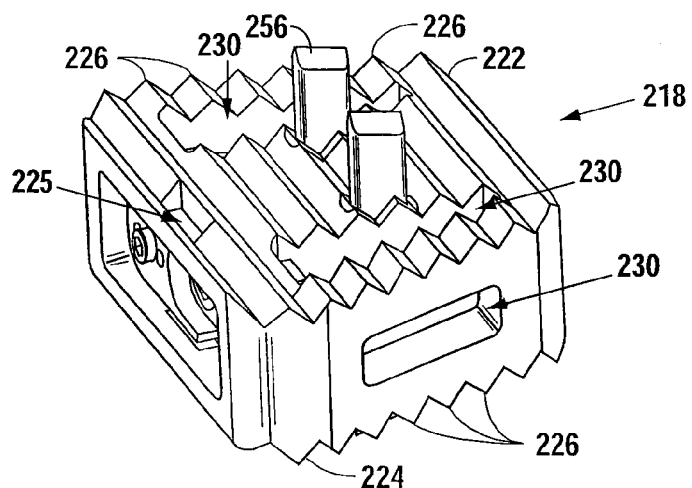
FIG. 11B is a rear isometric view of the third embodiment.

FIGS. 8A and 8B show the piston 132 of the second embodiment 118 in greater detail. The piston 132 has upper and lower angled surfaces 134, 136 angled approximately sixty degrees apart. Upper and lower grooves 148, 150 are formed longitudinally along the piston 132 from the faceplate 140 to the upper and lower angled surfaces 134, 136. Upper and lower grooves 148, 150 are alignable with, and during insertion guide the piston 132 along, upper and lower rails 144, 146 (see FIG. 7B) of the cage body 120. Shoulders 152 are formed in the piston body having a thickness T2. Engagement surfaces 153 are located between the shoulders 152 and the angled surfaces 134, 136.

FIGS. 9A and 9B show a titanium pin 156 and bushing 158, respectively, of the second embodiment 118 in greater detail. Each pin 156 has an angled engagement surface 160 that corresponds to the angle of the upper and lower angled surfaces 134, 136 of the piston 132 (see FIG. 8B). Each pin 156 tapers to a wedge 162 at the distal end. The upper end 166 of the bushing 158 corresponds in shape to the upper wall 122 (see FIGS. 7A-7C) such that, when assembled, the bushing 158 is flush with the ridges 126 of the upper surface of the cage body 120 (see, e.g., FIG. 10).

FIG. 10 is a perspective view of the second embodiment 118 with the pins 156 in an engaged position. During implantation, the angled engagement surfaces 160 (see FIGS. 9A-9B) of the pins 156 are contacted by and become flush with the upper and lower angled surfaces 134, 136 of the piston 132, which, as the piston 132 is inserted further into the cavity 128, causes the pins 156 to move through the channels 131, 133 to an engaged position. In this manner, engagement of the upper and lower angled surfaces 134, 136 with the pins 156 causes movement of the piston 132 into the cavity 128 to drive the pins 156 into the adjacent vertebra. The piston screw heads are positioned anterior of the posterior surface of the faceplate 140.

After insertion of the piston 132 is complete, each engagement surface 160 is flush with the engagement surfaces 153 of the piston to prevent the pins 156 from receding back into the cavity 128 and ensuring fastening of the pins 156 with adjacent bone matter. The upper and lower rails 144, 146 (see FIG. 7B) occupy the upper and lower grooves 148, 150, respectively, of the piston 132 to ensure proper alignment of the piston 132 within the cavity 128. The ridged bushings 158 are fitted within the upper and lower channels 131, 133 in the annular space between the pin 156 and channel walls to facilitate movement between disengaged and engaged positions.

Third Embodiment

A third embodiment 218 of the invention, shown in FIGS. 11-15, comprises a cage body 220 having upper and lower walls 222, 224 with ridges 226. Upper and lower walls 222, 224 partially define a cavity 228. Openings 230 through the upper and lower wall 222, 224 and sidewalls provide access to the cavity 228 to allow for bone growth thereinto from adjacent vertebrae. Upper and lower lock openings 225, 227 are formed through the upper and lower walls, 222, 224, respectively proximal to a piston opening in the posterior wall of the cage body 220.

A piston 232 having upper and lower angled surfaces 234, 236 is insertable into the cavity 228 through the piston opening. A screw 238 may thereafter be inserted through a piston faceplate 240 and secured to a screw mount 242 located at the posterior of the cavity 228. A locking plate 280 having a closed end 283 and an opened end 284 defined by upper and lower fingers 286, 288 is rotatably attached to the faceplate 240 with a locking member screw 282.

Figure 12A:
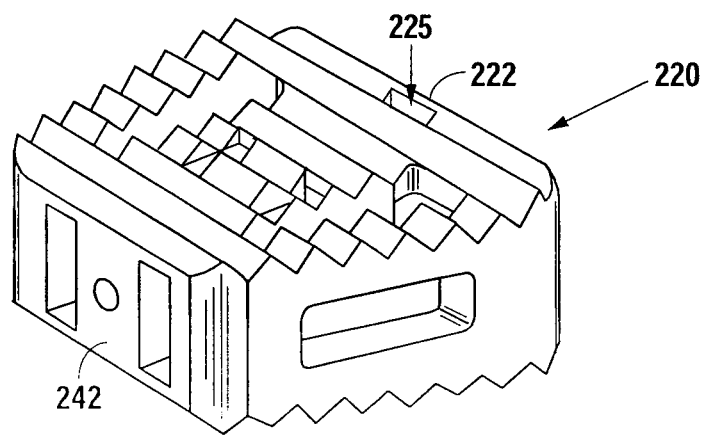
FIGS. 12A and 12B are a front isometric and a front view of the cage of the third embodiment.
Figure 12B:
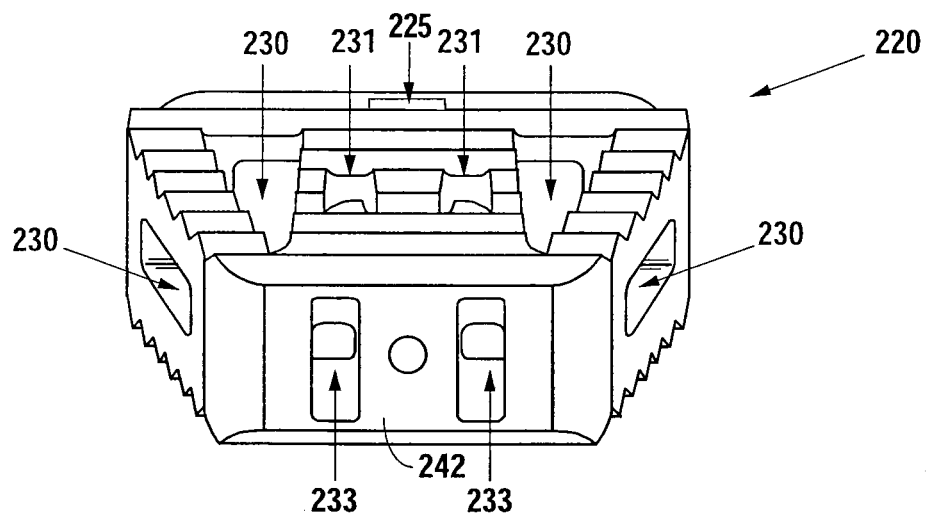

FIGS. 12A-12C show the cage body 220 in greater detail. A screw mount 242 is located near the front of the cavity 228. Openings 230 through the upper wall 222 provide access to the cavity 228 to allow for bone growth thereinto from adjacent vertebrae. Rectangular channels 231, 233 are located between the openings 230 and provide paths through the upper wall 222 and lower wall 224 to the cavity. As shown in FIG. 12C, upper and lower rails 244, 246 extend along the length of, and protrude into the cavity 228 from, the upper and lower walls 222, 224, respectively.

Figure 13A:
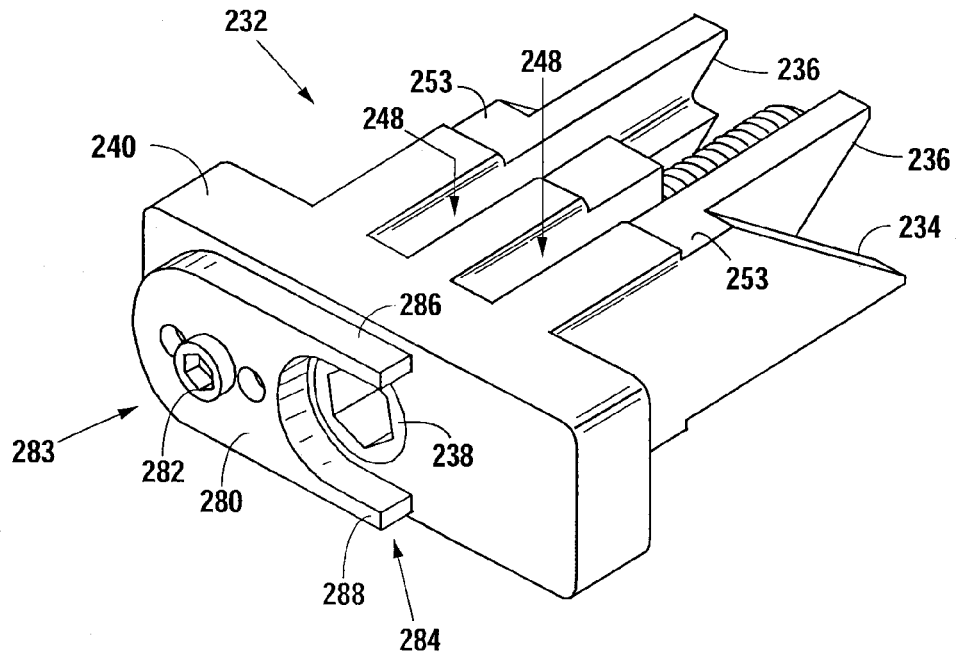
FIGS. 13A and 13B are rear and front isometric views, respectively, of the piston, locking plate, and piston screw of the third embodiment.
Figure 13B:
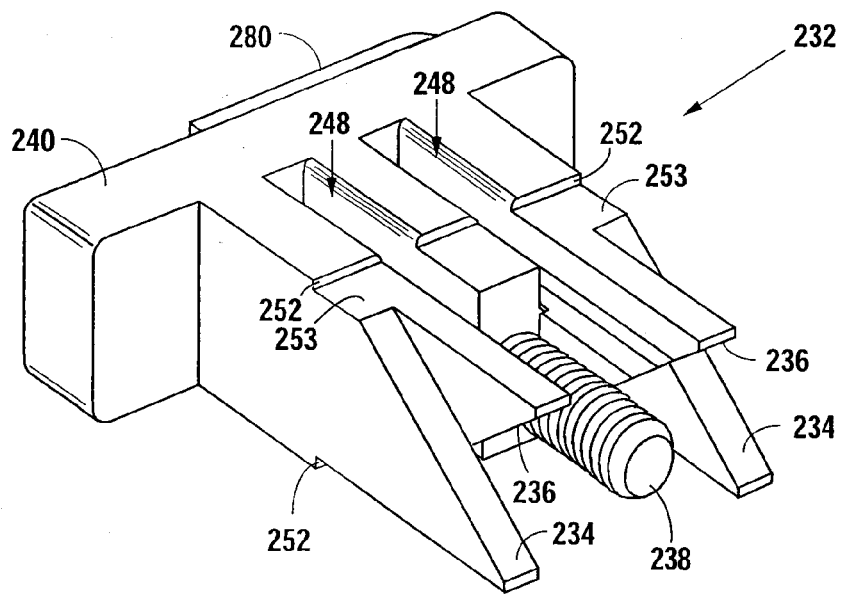
Figure 13C:
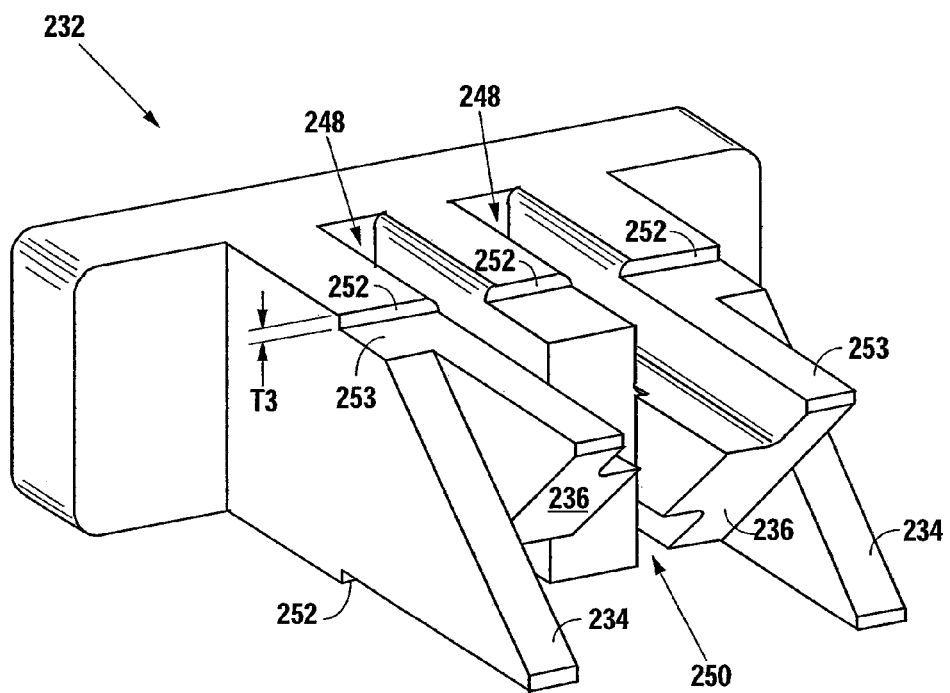
FIG. 13C is a front isometric view of the piston of the third embodiment.
Figure 14D:
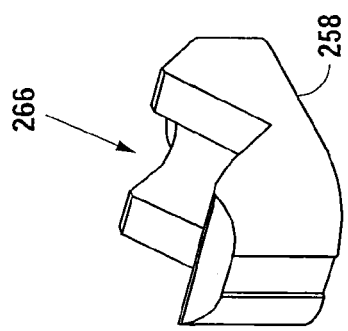
FIG. 14D is a bushing of the third embodiment.
Figure 14C:
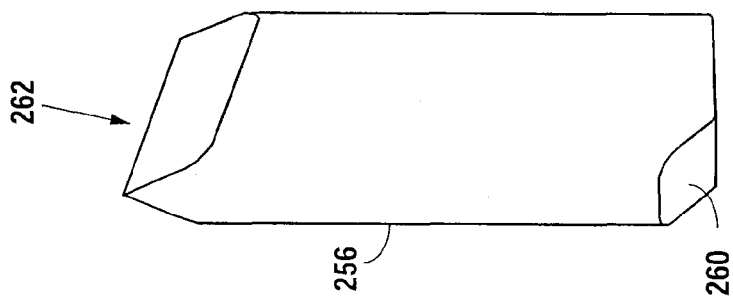
FIGS. 14A-14C are various views of the fastening member of the third embodiment.
Figure 14B:
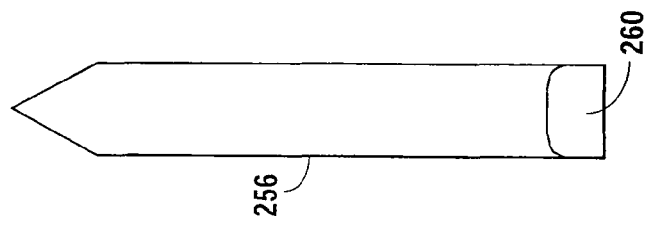
Figure 14A:
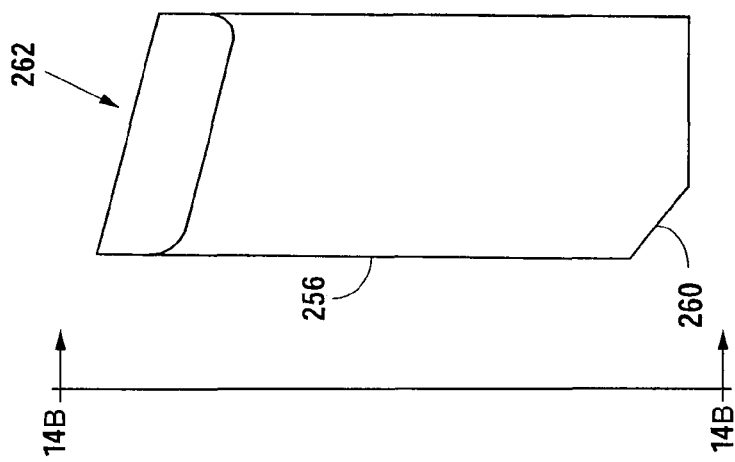

FIGS. 13A-13C show the piston 232, piston screw 238, and locking plate 280 of the third embodiment in greater detail. The piston 232 has upper and lower angled surfaces 234, 236 angled approximately sixty degrees apart. Upper and lower grooves 248, 250 are formed longitudinally along the piston 232 between the faceplate 240 and the upper and lower angled surfaces 234, 236. Upper and lower grooves 248, 250 are alignable with, and during insertion guide the piston 232 along, upper and lower rails 244, 246 (see FIG. 12C) of the cage body 220. Shoulders 252 are formed in the piston body having a thickness T3. Engagement surfaces 253 are located between the shoulders 252 and the upper and lower angled surfaces 234, 236.

FIGS. 14A-14D show a titanium pin 256 and bushing 258, respectively, of the third embodiment 218 in greater detail. Each pin 256 has an angled engagement surface 260 that corresponds to the angle of the upper and lower angled surfaces 234, 236 of the piston 132 (see FIG. 13C). Each pin 256 tapers to an angled wedge 262 at the distal end. The upper end 266 of the bushing 258 corresponds in shape to the ridged upper surface (see FIGS. 7A-7C) such that, when assembled, the bushing 258 is flush with the ridges 226 of the cage body 220 (see, e.g., FIG. 10).

FIGS. 15A-15C disclose rear, front, and side elevations, respectively of the third embodiment 218. During implantation, the angled engagement surfaces 260 (see FIGS. 14A-14C) are contacted by and become flush with the upper and lower angled surfaces 234, 236 of the piston 232, which, as the piston 232 is inserted further into the cavity 228, causes the pins 256 to move upwardly through the channels 231, 233 to an engaged position. In this manner, engagement of the upper and lower angled surfaces 234, 236 with the pin 256 causes movement of the piston 232 into the cavity 228 to drive the pins 256 into the adjacent vertebra.

After insertion of the piston 232 is complete, each engagement surface 260 becomes flush with the engagement surface 253 to prevent the nail from receding back into the cavity 228 and ensuring fastening of the nail 256 with adjacent bone matter. The upper and lower rails 244, 246 (see FIGS. 12A, 12C) occupy the upper and lower grooves 248, 250, respectively, to ensure proper alignment of the piston 232 within the cavity 228. The ridged bushings 258 are fitted within the channels 231, 233 in the annular space between the titanium pin 256 and channel walls to facilitate movement and retain the pins 256 in the channels 231, 233.

Figure 16A:
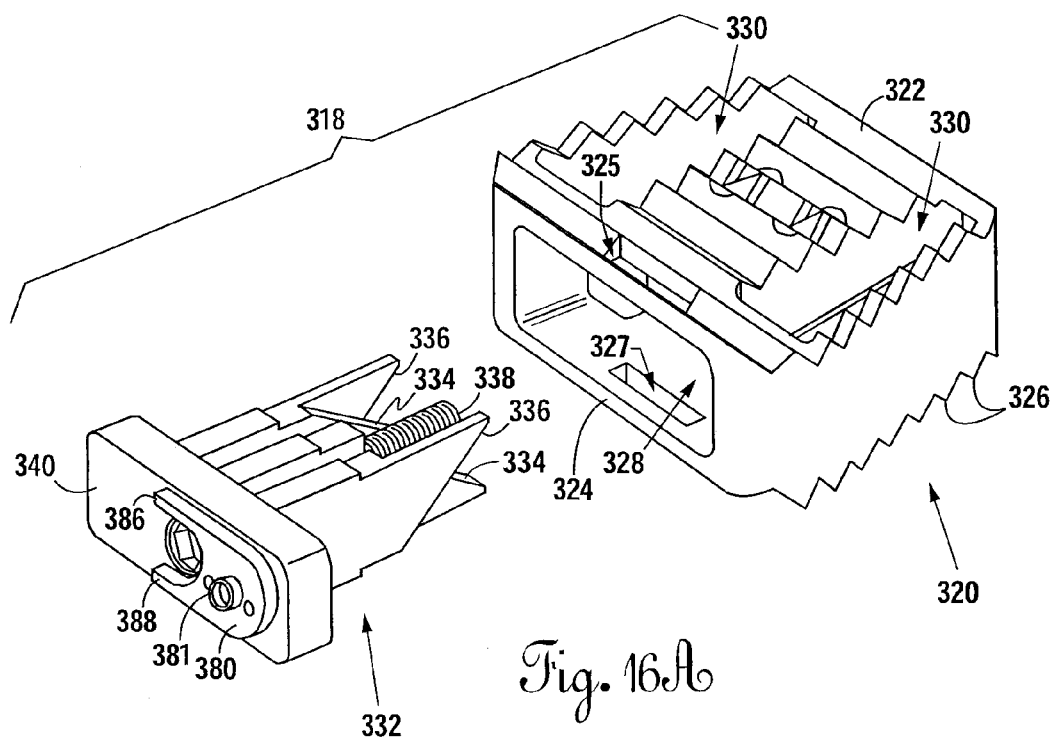
FIG. 16A is an assembly view of a fourth embodiment of the invention.
Figure 16B:
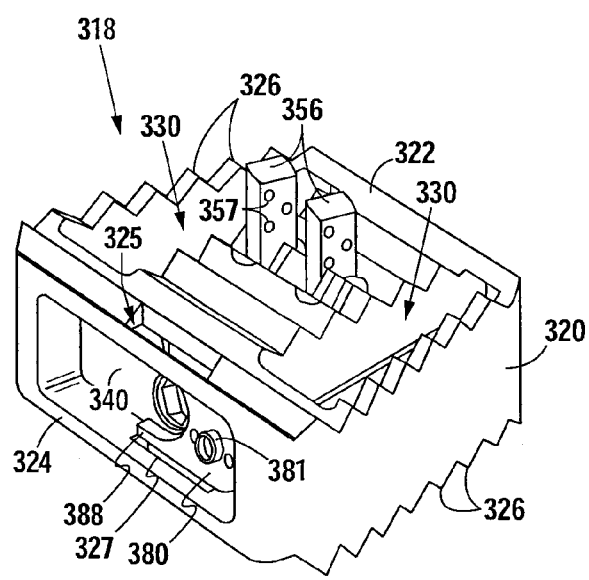
FIG. 16B is a rear isometric view of the fourth embodiment in an engaged state.
Figure 16C:
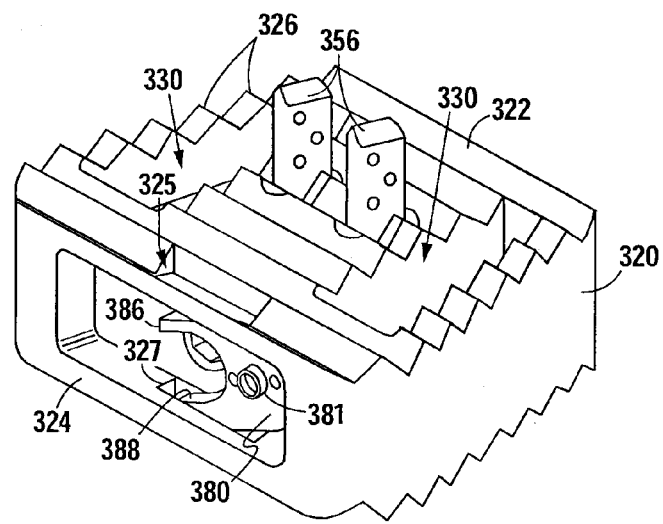
FIG. 16C is a perspective view of a fourth embodiment of Applicant's device.

Operation of the locking plate for this embodiment is identical to operation of the locking mechanism described hereafter with reference to the fourth embodiment Fourth Embodiment A fourth embodiment comprises a cage body 320, shown in FIGS. 16A-16C, comprises upper and lower walls 322, 324 with ridges 326. Upper and lower walls 322, 324 partially define a cavity 328. Openings 330 through the upper wall 322 provide access to the cavity 328 to allow for bone growth thereinto from adjacent vertebrae. Upper and lower lock openings 325, 327 are formed in the upper and lower walls 322, 324, respectively near the piston opening 328.

A piston 332 having upper and lower angled surfaces 334, 336 is insertable into the cavity 328. A screw 338 may thereafter be inserted through a piston faceplate 340 and secured to a screw mount located in the cavity 328. A locking plate 380 having a closed end 383 opened end 384 defined by upper and lower fingers 386, 388 is rotatably attached to the faceplate 340 with a screw 382. As shown in FIG. 16B, the fastening members of the fourth embodiment 318 comprises porous blades 356 with lateral passages 357 therethrough to allow bone growth.

FIG. 16B and FIG. 16C, which both depict the piston in an engaged position within the cage body 320, show the locking plate 380 in the unlocked and locked position, respectively. In the unlocked position, the screw 338 may be passed between the upper and lower fingers 386, 388, with the screw head accessible. Once the piston 382 is engaged with the cage body 320 to support the blades 356, the locking plate 380 is rotated around the locking plate screw 381 so that the lower finger 386 extends into the lower lock opening 325 and upper finger 386 covers the head of the piston screw 382. In this position, the locking plate 380 prevents "back out" of the piston screw 382 and piston 332, which assures engagement of the blades 356 with the adjacent vertebrae.

Although the embodiments of the present invention disclose titanium fastening members, alternative embodiments include stainless steel fastening members.

For each of the above-described embodiments, the upper and lower walls are at least substantially parallel. In alternative embodiments, however, the upper and lower walls may be angled relative to one another to correspond to curvature of the spine (e.g., to correspond to a lordotic curvature) at the targeted region of implantation. In such case, the front and rear sides will be of differing heights.

In addition to the nail and/or pins described hereinabove, alternative embodiments of the present invention contemplate a fastening member with a blade- or knife-like appearance, such as the porous blades shown in FIG. 17 and FIG. 20.

The present invention is described in terms of preferred illustrative embodiments of specifically described stand-alone spinal cages. Those skilled in the art will recognize that yet other alternative embodiments of such a device can be used in carrying out the present invention. Other aspects, features, and advantages of the present invention may be obtained from a study of this disclosure and the drawings, along with the appended claims.

I claim:

1. A spinal cage device for fusion of spinal vertebrae comprising:
   a cage body having upper, lower, and side walls that a define a cavity, said upper and lower walls having bone growth openings therethrough, said side walls including a posterior sidewall with a piston opening therethrough and an anterior sidewall;
   a piston having a piston body with anterior and posterior ends, said piston body being insertable along a longitudinal axis into said cavity through said piston opening, wherein said piston body comprise at least two angled surfaces adjacent to said anterior end;
   at least two fastening member channels extending through said upper and lower walls;
   at least two fastening members moveable within said at least two fastening member channels between a first disengaged position and a second engaged position;
     wherein in said second engaged position said at least two fastening members contact said piston body and are stationary relative to said cage body;
   at least one longitudinal guiding member extending into said cavity from at least one of said upper wall and said lower wall;
   at least two shoulder formed in the piston body, said at least two shoulder having a first thickness;
   at least two engagement surfaces positioned between said at least one shoulder and said at least two angled surfaces;
     wherein said at least two angled surfaces comprise a first angled surface angled at a first angle relative to a horizontal plane and a second angled surface angled at a second angle relative to said horizontal plane; and
     wherein said piston body defines at least one alignment groove formed longitudinally along said piston body and intersecting said anterior end.

2. The spinal cage device of claim 1, wherein said fastening members comprises a generally cylindrical nail having a nail head with a proximal surface and a distal end.

3. The spinal cage device of claim 1 further comprising:
   at least one screw mount positioned in the cavity;
   a faceplate connected to the posterior end of the piston body, said faceplate being insertable into the piston opening;
   at least one screw insertable through said faceplate and matable with said at least one screw mount.

4. The spinal cage device of claim 1, wherein the at least two angled surfaces adjacent to said anterior end of said piston comprise upper and lower angled surfaces, wherein said fastening members comprise an angled engagement surface corresponding to the angle of at least one of said upper and lower angled surfaces, said fastening members tapering to a wedge at their distal end.

5. The spinal cage device claim 1, wherein the at least two angled surfaces adjacent to said anterior end of said piston comprise upper and lower angled surfaces, wherein each of said upper and lower angled surfaces is longitudinally alignable with at least one of said fastening member channels.

6. The spinal cage device of claim 1 further comprising:
   at least one lock opening proximal to said piston opening; and
   a locking member.

7. The spinal cage device of claim 1, wherein said at least one fastening member is porous to allow bone growth therethrough.

8. The spinal cage device of claim 1, wherein either of the spinal cage or piston is made of PEEK or titanium.

9. The spinal cage device of claim 1, wherein the at least two fastening member channels of the cage body are located inside of the bone growth openings.

10. The spinal cage device of claim 1, wherein the cage body is configured such that the bone growth is unobstructed by the piston body and the fastening member.

11. The spinal cage device of claim 1, wherein the upper and lower walls of the cage body are angled relative to one another to correspond to the curvature of the spine at the targeted region for implantation.

12. A spinal cage device for fusion of spinal vertebrae comprising:
   a cage body having upper, lower, and side walls that a define a cavity, said upper and lower walls having bone growth openings therethrough, said side walls including a posterior sidewall with a piston opening therethrough and an anterior sidewall;
   a piston having a piston body with anterior and posterior ends, said piston body being insertable along a longitudinal axis into said cavity through said piston opening, wherein said piston body comprise at least two angled surfaces adjacent to said anterior end;
   at least two fastening member channels extending through said upper and lower walls;
   at least two fastening members moveable within said at least two fastening member channels between a first disengaged position and a second engaged position;
     wherein in said second engaged position said at least two fastening members contact said piston body and are stationary relative to said cage body;
   at least two shoulders formed in the piston body, said at least two shoulders having a first thickness;
   at least two engagement surfaces positioned between said at least one shoulder and said at least two angled surfaces;
     wherein said at least two angled surfaces comprise a first angled surface angled at a first angle relative to a horizontal plane and a second angled surface angled at a second angle relative to said horizontal plane;
   two lower guiding members member extending into said cavity from said lower wall;
   two upper guiding members extending into said cavity from said upper wall;
     wherein said piston body defines longitudinal grooves engagable with said guiding members; and
     wherein in said second engaged position said upper and lower guiding members are positioned within said longitudinal grooves.

13. The spinal cage device of claim 12, wherein said fastening members comprises a generally cylindrical nail having a nail head with a proximal surface and a distal end.

14. The spinal cage device of claim 12 further comprising:
   at least one screw mount positioned in the cavity;
   a faceplate connected to the posterior end of the piston body, said faceplate being insertable into the piston opening;
   at least one screw insertable through said faceplate and matable with said at least one screw mount.

15. The spinal cage device of claim 12, wherein the at least two angled surfaces adjacent to said anterior end of said piston comprise upper and lower angled surfaces, wherein said fastening members comprise an angled engagement surface corresponding to the angle of at least one of said upper and lower angled surfaces, said fastening members tapering to a wedge at their distal end.

16. The spinal cage device claim 12, wherein the at least two angled surfaces adjacent to said anterior end of said piston comprise upper and lower angled surfaces, wherein each of said upper and lower angled surfaces is longitudinally alignable with at least one of said fastening member channels.

17. The spinal cage device of claim 12 further comprising:
at least one lock opening proximal to said piston opening; and
a locking member.

18. The spinal cage device of claim 12, wherein said at least one fastening member is porous to allow bone growth therethrough.

19. The spinal cage device of claim 12, wherein either of the spinal cage or piston is made of PEEK or titanium.

20. The spinal cage device of claim 12, wherein the at least two fastening member channels of the cage body are located inside of the bone growth openings.

21. The spinal cage device of claim 12, wherein the cage body is configured such that the bone growth is unobstructed by the piston body and the fastening member.

22. The spinal cage device of claim 12, wherein the upper and lower walls of the cage body are angled relative to one another to correspond to the curvature of the spine at the targeted region for implantation.

23. A spinal cage device for fusion of spinal vertebrae comprising:
a cage body having upper, lower, and side walls that a define a cavity, said upper and lower walls having bone growth openings therethrough, said side walls including a posterior sidewall with a piston opening therethrough and an anterior sidewall;
a piston having a piston body with anterior and posterior ends, said piston body being insertable along a longitudinal axis into said cavity through said piston opening, wherein said piston body comprise at least two angled surfaces adjacent to said anterior end and a faceplate;
a screw and a screw mount;
at least two fastening member channels extending through said upper and lower walls;
at least two fastening members moveable within said at least two fastening member channels between a first disengaged position and a second engaged position;
wherein in said second engaged position said at least two fastening members contact said piston body and are stationary relative to said cage body;
at least one lock opening proximal to said piston opening;
a locking member rotatably-connected to said faceplate; and
wherein said locking member comprising a body portion rotatably-connected to said faceplate and at least one finger extending from said body portion;
wherein in said second engaged position said locking member is rotatable to a locked position in which a portion of said locking member extends into said at least one lock opening and a portion of said locking member is positioned adjacent said screw;
wherein in said second engaged position said at least one finger is positioned in said lock opening and adjacent said screw.

24. The spinal cage device of claim 23, wherein said fastening members comprises a generally cylindrical nail having a nail head with a proximal surface and a distal end.

25. The spinal cage device of claim 23, wherein the at least two angled surfaces adjacent to said anterior end of said piston comprise upper and lower angled surfaces, wherein said fastening members comprise an angled engagement surface corresponding to the angle of at least one of said upper and lower angled surfaces, said fastening members tapering to a wedge at their distal end.

26. The spinal cage device claim 23, wherein the at least two angled surfaces adjacent to said anterior end of said piston comprise upper and lower angled surfaces, wherein said fastening member comprises an angled engagement surface corresponding to the angle of at least one of said upper and lower angled surfaces, said fastening member tapering to a wedge at its distal end; and wherein each of said upper and lower angled surfaces is longitudinally alignable with at least one of said fastening member channels.

27. The spinal cage device of claim 23 further comprising:
at least one lock opening proximal to said piston opening; and
a locking member rotatably-connected to said faceplate;
wherein in said second engaged position said locking member is rotatable to a locked position in which a portion of said locking member extends into said at least one lock opening and a portion of said locking member is positioned adjacent said screw.

28. The spinal cage device of claim 23, wherein said at least one fastening member is porous to allow bone growth therethrough.

29. The spinal cage device of claim 23, wherein either of the spinal cage or piston is made of PEEK or titanium.

30. The spinal cage device of claim 23, wherein the at least two fastening member channels of the cage body are located inside of the bone growth openings.

31. The spinal cage device of claim 23, wherein the cage body is configured such that the bone growth is unobstructed by the piston body and the fastening member.

32. The spinal cage device of claim 23, wherein the upper and lower walls of the cage body are angled relative to one another to correspond to the curvature of the spine at the targeted region for implantation.

\* \* \* \* \*